(12) United States Patent
Solomon et al.

(10) Patent No.: US 8,506,999 B2
(45) Date of Patent: *Aug. 13, 2013

(54) PHARMACEUTICAL TABLETS COMPRISING A PLURALITY OF SEGMENTS

(75) Inventors: Lawrence Solomon, Boca Raton, FL (US); Allan S. Kaplan, Boca Raton, FL (US)

(73) Assignee: ACCU-BREAK Technologies, Inc., Plantation, FL (US)

( * ) Notice: Subject to any disclaimer, the term of this patent is extended or adjusted under 35 U.S.C. 154(b) by 187 days.

This patent is subject to a terminal disclaimer.

(21) Appl. No.: 12/979,230

(22) Filed: Dec. 27, 2010

(65) Prior Publication Data

US 2011/0142932 A1 Jun. 16, 2011

Related U.S. Application Data (63) Continuation of application No. 10/598,344, filed as application No. PCT/US2005/018632 on May 23, 2005, now Pat. No. 7,879,352.

(51) Int. Cl.
*A61K 9/44* (2006.01)

(52) U.S. Cl.
USPC .......................... 424/467; 424/465; 424/472

(58) Field of Classification Search
USPC .......................................................... 424/467
See application file for complete search history.

*Primary Examiner* — Jake M. Vu (74) *Attorney, Agent, or Firm* — Ted W. Whitlock (57) ABSTRACT

Deeply scored pharmaceutical tablets are disclosed, along with pharmaceutical tablets with a score in a segment that adjoins a segment lacking a pharmacologically effective dose of any drug.

9 Claims, 3 Drawing Sheets

PHARMACEUTICAL TABLETS COMPRISING A PLURALITY OF SEGMENTS

This is a continuation of U.S. patent application Ser. No. 10/598,344 filed Apr. 4, 2008 now U.S. Pat. No. 7,879,352, which is a national stage application filed pursuant to 35 USC 371, claiming the benefit of and/or priority to International Patent Application PCT/US05/018632 filed May 23, 2005.

FIELD OF THE INVENTION

The invention is concerned with layered, immediate release pharmaceutical tablets that preferably contain a deeply scored segment that adjoins a pharmacologically inactive segment.

BACKGROUND OF THE INVENTION

Scoring of pharmaceutical tablets is well known. Scoring of pharmaceutical tablets produced in a layered fashion is also known, but has been employed less extensively. Scores into a tablet have not exceeded 1 mm in depth. Even though inaccurate breaking of scored tablets is a well-known problem, attention has not been paid to solving this problem by creating segmented (e.g., layered) tablets in a tablet press with a segment that provides some or most of said breaking region when the tablet is broken, and pari passu provides physical support for the part of the tablet with the deep score. The scope of the problem with tablet breaking may be summarized, in part, as follows: Many drugs require dosage adjustments, such as warfarin, the scored tablets of which are frequently broken. These dosage adjustments through tablet breaking by patients have been determined to be imprecise. As the following discussion demonstrates, for many years experts have called upon the pharmaceutical industry to improve the quality of tablet breaking, yet such has not been optimized until the current invention.

In 1984, Stimpel et al. ("Stimpel"), described the relative accuracy of breaking of various tablets for treatment of cardiovascular problems. M. Stimpel et al., "Breaking Tablets in Half." *The Lancet* (1984):1299. Even though breaking was performed by a sophisticated, dexterous person, Stimpel found that breaking was not accurate, and opined that real world use by patients would provide yet more unsatisfactory results. Stimpel called upon the pharmaceutical industry to improve the accuracy of splitting tablets: "Clearly any assumption that halving a tablet will not lead to inaccurate doses is invalid. This potential source of inaccuracy could be even more significant in clinical situations (our study was done under ideal conditions) and the pharmaceutical industry should tackle it, either by improving divisibility (as already has been done for lopressor and logroton) or, even better, by marketing a wider range of unscored tablets to provide all the doses that might be indicated clinically."

Despite that finding and statement, and despite the issuance of various patents relating to optimizing a scoring pattern and/or tablet shape, Rodenhuis et al., (2004) noted that: "Improving the functioning of score lines may be a more practical approach than banning this dosage form." N. Rodenhuis et al. (emphasis added), "The rationale of scored tablets as dosage form." *European J. of Pharmaceutical Sciences* 21 (2004):305-308 (hereafter "Rodenhuis"). Rodenhuis observed that European regulatory authorities started a policy to discourage scoring of tablets in 1998. This policy change, according to Rodenhuis, likely related to "many recent reports of bad functioning score lines," that "many scored tablets are difficult to break," and that "many scored tablets show unsatisfactory mass uniformity of the subdivided halves." The authors then go on to describe useful aspects of scoring tablets. For a comprehensive review article on this topic, see van Santen, E., Barends, D. M. and Frijlink, H. W. "Breaking of scored tablets: a review." *European J. of Pharmaceutics and Biopharmaceutics* 53 (2002):139-145.

Some current studies that demonstrate the severity of the problem are described below.

Peek et al., (2002), studied tablet splitting by "elderly patients" aged 50-79. Peek, B. T., Al-Achi, A., Coombs, S. J. "Accuracy of Tablet Splitting by Elderly Patients." *The Journal of the American Medical Association* 288 No. 4 (2002): 139-145. Breaking scored tablets with mechanical tablet splitters without specific instruction led to highly unsatisfactory separating of the tablets. For example, warfarin 5 mg was on average split into 1.9 and 3.1 mg tablets. This potent anticoagulant has such a narrow therapeutic range that 2, 2.5, and 3 mg tablet doses are manufactured. Biron et al., (1999), demonstrated that warfarin 10 mg also often split to less than 4.25 or greater than 5.75 mg. Biron, C., Liczner, P., Hansel, S., Schved, J. F., "Oral Anticoagulant Drugs: Do Not Cut Tablets in Quarters." *Thromb Haemost* 1201 (1999). In addition, they demonstrated that loss of mass due to crumbling or chipping or the breaking of the warfarin tablets was statistically significant. They also demonstrated that quartering of the tablets was grossly inaccurate.

McDevitt et al., (1998), found that 25 mg unscored hydrochlorothiazide (HCTZ) tablets were manually split badly enough that 12.4% deviated by more than 20% from ideal weight. McDevitt, J. T., Gurst, A. H., Chen, Y. "Accuracy of Tablet Splitting." *Pharmacotherapy* 18 No. 1 (1998):193-197.77% of the test subjects stated that they would be willing to pay a premium for individually produced 12.5 mg HCTZ tablets rather than split unscored 25 mg tablets.

Rosenberg et al., (2002), studied pharmacist-dispensed split tablets. Rosenberg, J. M., Nathan, J. P., Plakogiannis, F. "Weight Variability of Pharmacist-Dispensed Split Tablets." *Journal of American Pharmaceutical Association* 42 No. 2 (2002):200-205. They found that "tablet splitting resulted in an unacceptably high incidence of weight variation." They recommended that "standards should be developed to ensure uniformity of split tablets."

Teng et al., (2002), using a trained individual in a laboratory setting to split tablets, concluded that "the majority of the 11 drug products we tested, when assessed for their ability to be split into half-tablets of equal dose, failed a liberally interpreted USP (United States Pharmacopeia) uniformity test . . . . The practice of dividing tablets to save costs or to improve a dosage regimen . . . is not recommended for patients using drugs with more substantial toxicity and steep dose-response efficacy curves." Teng, J., Song, C. K., Williams, R. L., Polli, J. E. "Lack of Medication Dose Uniformity in Commonly Split Tablets." *Journal of American Pharmaceutical Association* 42 No. 2 (2002):195-199.

Rodenhuis reported that 31% of all tablets in one Netherlands study were subdivided before being swallowed. In the U.S., many "managed care" insurance organizations encourage tablet splitting by patients of tablets that are often unscored and that may be irregularly shaped.

Many drug products in the US are either unscored or are provided as capsules despite being able to be produced as tablets. The invention herein provides a solution for bath scored and unscored tablets that provides an improved solution to the problems described above.

The current invention aims to ameliorate the above problem by providing, inter ails novel, deep scores into a segment of a tablet that contains an active ingredient for which enhanced precision of dosing with a dose less than that present in the whole tablet is desired, as well as providing novel use of pharmacologically inactive segments as part of a bilayer immediate release compressed tablet.

Embodiments of the invention describe an immediate release compressed pharmaceutical tablet with an outer segment (e.g., a layer) that is not provided with a pharmacologically effective amount of any active pharmaceutical ingredient, said tablet containing a segment having a pharmacologically effective quantity of an active pharmaceutical ingredient and a score to locate and aid tablet division. The prior art discloses outer layers of layered pharmaceutical tablets under only two circumstances: as part of a controlled-release product, as with Uroxatral®, or for specialized purposes in which a molded part of a tablet may be inactive, but said tablet is not provided with a score as it is not disclosed to be adapted to be split into a plurality of smaller dosage forms. Published U.S. Application 2005/0019407A1 describes a composite dosage form which has first and second portions joined at an interface. These dosage forms have a first molded material and a second compressed material. There is no disclosure of any modification of the disclosed dosage forms that would facilitate the breaking of the dosage forms into any subdivided form.

The present invention is concerned with segmented pharmaceutical dosage forms that are adapted for breaking through more than one segment. Until now, a score in tablets has had practical limitations, because a deep score, such as one that extends through 85% of the height of a tablet, would tend to lead to structural instability of the tablets, so that they would tend not to survive intact the production and transport processes. The invention has as a primary object utilizing a layered segment of a tablet that provides structural support for a segment of the tablet derived from a granulation provided with an active pharmaceutical agent.

SUMMARY OF THE INVENTION

The present invention provides a compressed immediate release pharmaceutical tablet core structure which comprises at least two segments wherein:
(a) a first scored segment contains a pharmacologically effective amount of a drug or drugs and;
(b) a second segment, that adjoins said first segment, wherein said second segment contains from an undetectable amount to a maximum of 80% of the concentration of the same drug or drugs in said first segment. In the case in which said first and second segments are the only segments in the tablet, and said second segment contains a pharmacologically ineffective quantity of any active drug, then any score in said first segment is novel and said second segment aids the structural integrity of the tablet, as well as aiding in minimizing loss of mass during tablet breaking.

The concentration of a drug or drugs in a segment means, herein, the ratio, on a weight to weight basis, of the drug or drugs in said segment to the total weight of said segment, which includes said drug or drugs and inactive excipients.

A preferred aspect of the invention is a pharmaceutical tablet having two or more segments, wherein a first segment includes a pharmacologically effective amount of a drug or drugs and has a score that extends into said first segment from 70% to 99.5% of the distance from a surface of said first segment towards an opposite face (surface) of said first segment having on said opposite face, an adjoining second segment. In a preferred embodiment, said second segment has an undetectable amount of drug up to a maximum of 80% of the concentration of the drug in said first segment.

A preferred embodiment of the invention involves a two segment tablet, formed from a first granulation comprising inactive excipients and a second segment formed from a granulation comprising active drug, preferably in a therapeutically effective quantity. In this embodiment, special care is taken to manufacture said second segment with a score that extends nearly completely through said second segment, so that breaking said tablet through the bottom of said score creates two new tablets with a largely or substantially predetermined quantity of active drug in each new, smaller tablet structure denoted a tablette herein.

The score may extend up to but not into the first segment.

A tablette is formed when a tablet or larger tablette is broken. Typically tablets of the invention, when broken intentionally by an end user, are intended to be broken in half through a score. Assuming successful tablet breaking, two major tablet fragments will be created, each of which is a tablette. Crumbs and small chips that are formed incidental to the breaking process are not considered to be tablettes.

Another most preferred embodiment involves utilizing the above-described tablet as a core structure of a larger tablet, so that in this embodiment a most preferred tablet may contain three segments, each derived from the following granulations: a first segment is derived from a granulation containing drug and is deeply scored, a second is the middle segment and is derived from an inactive granulation, and a third segment is derived from a granulation containing drug and is optionally scored as well. In said tablet, the layers are arranged ("disposed") vertically one on top of another, and the first or third segment (or both) contains a deep score that most preferably extends over 90% of the way through said segment to nearly reach said middle segment. The active ingredients comprising said first and third segments may be identical or different and are not limited.

Other embodiments, including less preferred embodiments, are discussed subsequently.

BRIEF DESCRIPTION OF THE DIAGRAMS

DETAILED DESCRIPTION OF THE INVENTION

Before describing the present invention in detail, it is to be understood that this invention is directed to pharmaceutical tablets, preferably those pharmaceutical tablets which are made by compression such as by compression applied in a die in an automated tabletting machine, and preferably those pharmaceutical tablets that are uncoated. It is also to be understood that in describing and claiming the present invention, the following terminology will be used in accordance with the definitions set out below for the purpose of providing a general understanding and is not intended to be limiting.

A "segment" represents the entirety of a substantially homogeneous contiguous region of a tablet or tablette (see below) of the invention. Segments are formed from layers, which are formed from granulations. If two substantially identical granulations entered the die sequentially, one on top of the other, thus forming two layers, and were compressed together, a compound segment, i.e. one formed from more than one substantially identical layer would be formed. If, however, two granulations containing different active drugs, were compressed one onto the other, the two granulations would form two segments. Granulations comprising the same active drug but with dissimilar excipients would also comprise two segments if one granulation were compressed onto another.

A compressed layer that is not adjacent to a layer formed from a substantially identical granulation that formed said first-mentioned layer is denoted a "simple segment." Tablets of the invention comprise, without limitation, two or more segments, and each segment may be formed from two or more layers, though more typically in the invention a segment will be formed from one layer and not a plurality of layers.

A "layer" is a tablet structure that is made by introducing an amount of an individual granulation into a tablet die to fill at least a part of the die. A layer is considered to be present whether it is in the form of an un-tamped, tamped or fully compressed granulation. Because some powder migration of material may take place between granulations and layers in the tabletting machine, some amounts of granulations forming a layer may be transferred to another layer or all other layers; in the most preferred embodiments of the invention, such an effect is not pharmacologically significant.

The terms "active agent," "active drug," "drug," "active pharmaceutical ingredient" and "pharmacologically active agent" are interchangeable herein and refer to a chemical material or compound which, when administered to an organism (human or animal) induces a pharmacological effect, and which includes prescription and non-prescription pharmaceutical compounds, as well as pharmacologically effective doses of vitamins, co-factors and the like. Not considered to be drugs herein are such substances as foodstuffs and vitamins in "recommended daily allowance" quantities.

The term "interface" refers to that part of the tablet representing the region at which two segments adjoin one another.

The term "undetectable amount" means that using conventional analytical techniques such as high performance liquid chromatography (HPLC), nuclear magnetic resonance imaging (NMRI) and the like, the presence of an active compound cannot be detected. The term "pharmacologically ineffective amount" means that any amount of drug detected has no detectable pharmacological effect. It is understood that due to the conditions under which high speed automated tabletting equipment are operated, some unintentional mixing of different granulations may occur which may cause some amounts of one granulation to appear in a segment where it was not intended to be placed.

The terms "horizontal," "transverse," and "vertical" when used in relation to a tablet, are based on the spatial orientation of the tablet as, and after, it is produced in a die, but before removal or ejection from the die.

Tablets of the invention are most conveniently manufactured, for commercial or research use, on a high-speed tablet press that has a plurality of filling stations. A tablet press provided with exactly two filling stations is typically referred to as a bilayer press; a tablet press provided with exactly three filling stations is typically referred to as a tri-layer press, etc. A "five-layer" press is commercially available (Korsch AG, Germany). Some tablets of the invention may be manufactured on a bilayer press, and others require a tri-layer or a five-layer press.

Tablets of the invention may be manufactured using one granulation comprising a drug or mixture of drugs and a second granulation containing optionally an undetectable amount of drug or a pharmacologically ineffective amount of drug, or containing the same drug or drugs, or a different drug or drugs. The basic most preferred tablet of the invention may be produced with different techniques.

Figure 1:
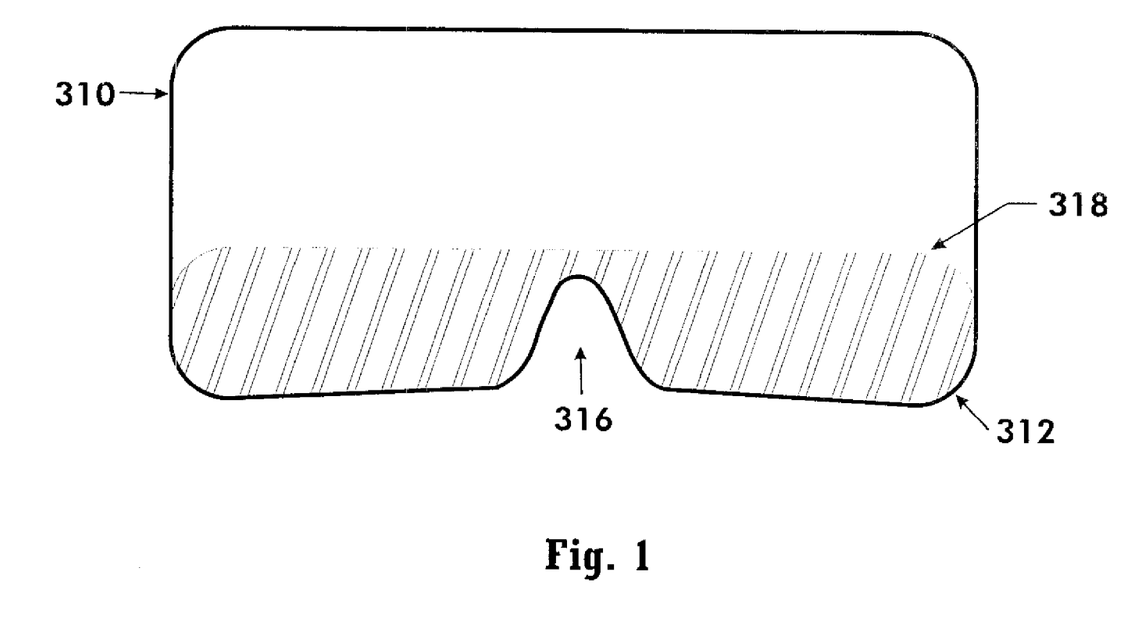
FIG. 1 depicts a tablet with two segments and one score.

For example, FIG. 1 demonstrates a bilayer tablet. Production may involve first allowing a granulation containing active drug into a die that has an embossed lower punch, so that said granulation forms an undivided layer indented from below by said embossing. Said embossing is not limited in its pattern. After optional and preferred tamping, an inactive granulation enters the die and after optional pre-compression, a tablet is formed by final, full-force compression. This compression pushes the first, lower layer almost to the level of the uppermost aspect of the embossing, so that an especially deep score may be produced. Each granulation, after entry into the die, forms a layer. After final compression of the tablet, each layer may also be referred to as a segment of the tablet. Except for inadvertent mixing between granulations, the upper segment is inactive, so that tablet breaking may occur substantially through the inactive segment, thus providing substantial improvement over existing methods of scoring tablets from the standpoint of accuracy of subdividing a dose. Less preferably, the second granulation could contain a diluted quantity of the active ingredient or ingredients comprising said first granulation. Such a maneuver would be useful if it were difficult to place adequate drug substance entirely within said first granulation.

Additional preferred embodiments flow from the first example immediately above. In the case in which there were a desire to provide additional active drug in a segment above the deeply scored segment, a trilayer design could be useful, given certain practical limitations regarding the height of embossings. In this example, a highly concentrated granulation of drug forms the first granulation, which is pushed as close to the top of the embossing as possible; a second, less concentrated (w/w %) granulation comprising the identical active ingredient enters the die, and a third, inactive granulation finally enters the die. After final compression, a tablet that is preferably very deeply scored with respect to the first segment has been created, and the middle segment, which will tend to break more accurately than the outer segment, improves the accuracy of said tablet breaking relative to a tablet of simpler design.

Another preferred embodiment related to the first example is as follows. A first active granulation enters the die onto an embossed lower punch and is tamped. A second, inactive granulation enters the die and the second filling station and again at the third filling station, and is optionally and preferably tamped after each of said granulations enters said die. At a fourth filling station, a different granulation from the first enters the die, is optionally and preferably tamped, and then final compression takes place, pushing said first granulation lower into the die so that the uppermost part of said first granulation remains above the uppermost part of said embossing. Thus, said first granulation has formed an undivided layer. In this example, the use of two identical granulations to form two layers that are compositionally substantially identical may be useful to form one tall segment. Such a segment, whether formed from two or more substantially identical inactive granulations or ones comprising an active drug or drugs, is called a compound segment herein. The utility of the dosage form is that it allows different active drugs to primarily be placed in opposite ends of a "taller than wide" tablet, so that both drugs may be given together in a whole tablet, but said tablet also may be broken through a middle segment to create two tablettes comprising substantially different drugs (ignoring any inadvertent mixing between granulations). The current invention is most usefully employed after such optional tablet breaking through said middle segment, after which the first segment may then be itself subdivided if desired to create a plurality of accurately dosed tablettes.

The above example could as easily utilize a granulation compositionally substantially identical to said first granulation to enter (again) at the fourth filling station. Further segments could be added as a fifth segment and beyond, technical capacity for tablet production being the limiting factor. Furthermore, said second segment could comprise an active drug, or a mixture of the drug or drugs present in both the first and third segments in the example above, and the utility of the invention would persist, though relevance in medical or veterinary practice would relate to the nature of the drug or drugs in said middle segment.

A less preferred embodiment is as follows. A first granulation comprising a drug enters into a tablet die. An embossing that is 0.3 mm high bisects the lower punch. A second, inactive granulation enters said die above said first granulation. The tablet is compressed. The first segment is one (1.0) mm high after final compression. Thus the score is 30% of the way through said first segment. The tablet has immediate release characteristics. The tablet is novel but lacks substantial advantages over tablets known in the art that lack a substantially inactive segment, but the second segment does provide structural support for the tablet, so there may be some advantage.

The invention thus teaches novel methods of manufacture of deep scores within pharmacologically active parts of the tablet. Preferred methods of manufacture of the tablets of the invention that utilize an embossed bottom punch to produce the scored segment that is the subject of the invention utilize an upper punch that does not have any embossing, or else has an embossing of a small vertical dimension, above the embossing present on and extending upwards from the base of said lower punch.

A different mode of manufacture may be employed, using an embossed upper punch and a preferably flat-faced lower punch. In this technique, a most preferred tablet of the invention may be produced as follows. A first, inactive granulation enters the die and is optionally tamped. A second granulation comprising drug then enters the die, is optionally tamped, and final compression occurs. Some amount of drug lies between the lower part of said embossing but the bulk of second granulation is apart from the breaking area, and thus when and if force is applied in a conventional, vertical fashion to the lowest aspect of the score, highly accurate tablet breaking will take place with respect to the active drug.

Tablets of the above design are not limited to two segments. A segment represents a contiguous part of a tablet of the invention that is formed from one granulation entering the tablet die at a time, with exceptions such as the following: If two successive granulations comprised the same active drug and similar excipients, then when compressed, they would comprise one segment. If, however, two different active drugs, such as different active drugs or different salts of the same active drug, were compressed onto each other, they would comprise two segments. Granulations comprising the same active drug but with dissimilar excipients would comprise two segments if one granulation were compressed onto another.

As used herein, such terms as "horizontal" ("transverse") and "vertical" when used in relation to a tablet, are based on the spatial orientation of the tablet as, and after, it is produced in a die, but before removal or ejection from the die. Current methods of manufacture produce tablets with one granulation entering the die on top of another, so that tablets of the invention produced in such a manner comprise one or more top (outer) segments, one or more bottom (outer) segments, and optionally one or more middle (inner) segments. A segment that is not a top or bottom (i.e., outer) segment is considered to be an inner segment.

If a tabletting machine were developed that allowed tablet manufacture to occur so that separate granulations could be sequentially placed in a die horizontally (side-to-side) and not vertically as is currently the practice, then the tablets so produced would be within the scope of the present invention as the same product would be produced.

Tablets of the invention are limited as to the dimension of the tablet, nature or number of active ingredients, type of excipients, or depth of the score. The depth or height of the score reflect the dimensions of said embossings. Conventional embossings are less than one (1) mm in vertical dimension from the adjacent base of the punch on which the embossings are placed. Embossings of the current invention are not limited in height. In practice, three (3) mm may be a practical upper limit for the height of an embossing.

A technique to provide a deep score is to cut into a tablet, such as with a knife or a high-speed cutting apparatus, at a desired location on the tablet. The tablets of the invention are best broken transversely in order to realize their benefits. They may be broken in standard ways, according to the invention such as either by applying force such as a cutting edge directly to the desired breaking region, or to other areas of the tablet to realize the same effect.

Figures 2A, 2B:
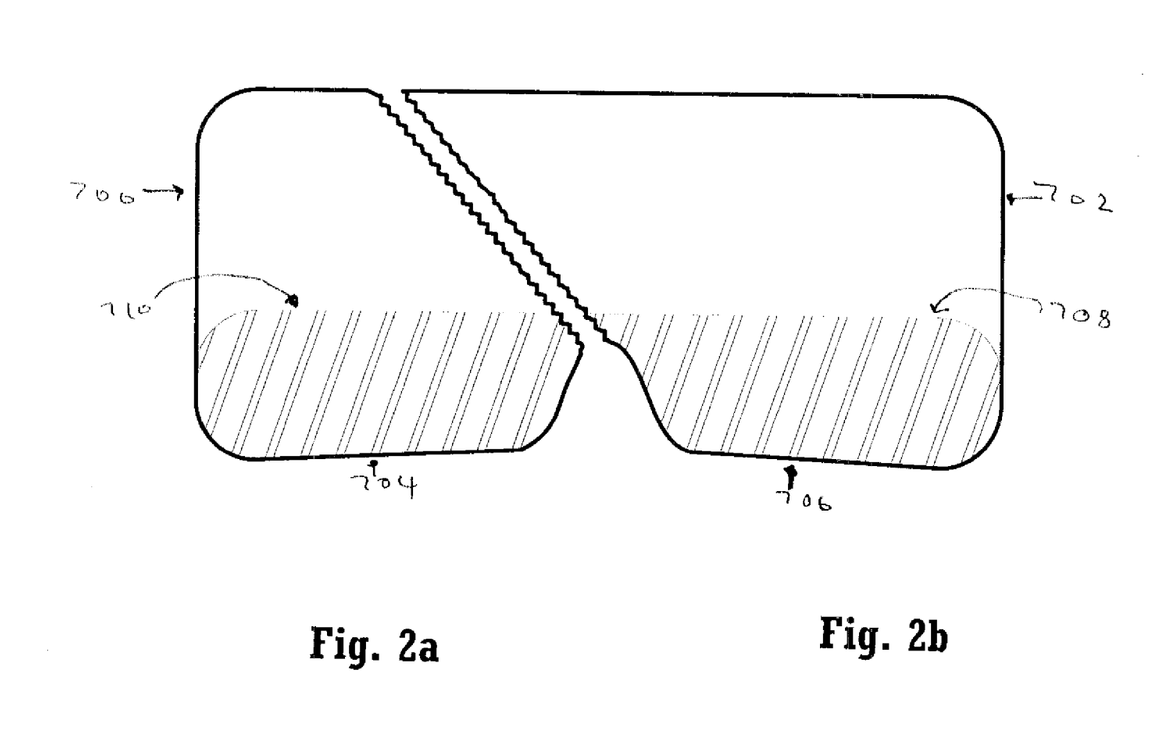
FIG. 2 depicts two tablettes, each with two segments.
Figure 3:
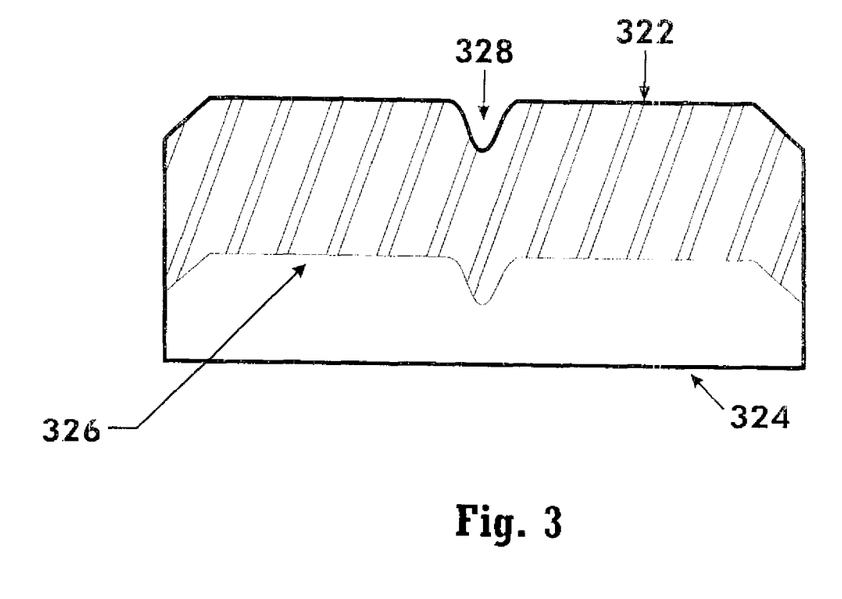
FIG. 3 depicts a tablet with two segments and one score.

FIGS. 1-3 depict cross-sectional views of tablets and tablettes of the invention. All views are front views.

The drawings depict vertical cross sectional views of tablets and tablettes of the invention. Tablets are depicted as if they were in the die, so that the top of the tablet as it is oriented on the page corresponds with the top of the tablet in the die. In other words, the top segment of the tablet as viewed contains the last granulation to enter the die. Tablettes are depicted as they would have been in the die before they were separated from the intact tablet.

"Front views" refer to a cross-sectional view of a tablet that has a theoretical geometric plane passed through the tablet relative to a side which is arbitrarily designated as the front. Figures labeled as "side view," which also have a corresponding "front view" are taken as a cross-section through the whole tablet from the right side of a front view i.e., a side view is a cross-section that is taken by passing a plane through the vertical axis of the whole tablet at a 90° angle to the cross-sectional front view. Each front view represents a schematic cross-section that passes through the midpoint of the horizontal cross-section as measured from the front of the tablet to the back of the tablet or tablette. The front view is also parallel to the major axis of the tablet (e.g., for a tablet with a rectangular (but not square) transverse cross-section, the longer side of the perimeter is parallel with the plane that depicts the cross-sectional, front view. That plane is located half-way between the front and back surfaces of said tablet.

Tablettes are also depicted as they would exist in relation to the tablet die in which they are formed.

The upper part of each figure corresponds to the upper part of a tablet, all of which are depicted as they are situated within a die after final compression and before ejection from the die. For consistency, tablettes are depicted in the same orientation as the tablets from which they are formed, although tablettes are created after tablet formation and ejection from the die.

Tablettes are depicted with broken surfaces as indicated by a fine saw-tooth pattern. Such saw-tooth depiction is schematic and not intended to represent the actual pattern of breaking of a tablet.

FIG. 1 depicts an immediate release tablet with a score 316 that extends approximately 90% through the bottom segment 312. Upper segment 310 allows structural stability of the tablet despite the deep score 316. In this tablet, no pharmacologically effective dose of the drug present segment 312 is present in segment 310. In another preferred embodiment, segment 310 may contain a different drug than is present in segment 312, preferably in a pharmacologically effective quantity. In a less preferred embodiment, segment 310 contains a pharmacologically effective quantity of the drug or drugs present in segment 312, but in a diminished concentration relative to the excipients in each segment. Interface 318 is present.

Breaking the tablet of FIG. 1 gives two tablettes as shown in FIG. 2. Largely inactive segment 310 of FIG. 1 has been divided into two segments, 700 in the smaller tablette as shown in FIGS. 2a and 702 in the larger tablette of FIG. 2b. Even though breaking as demonstrated is far from vertical, it is clear that the amount of drug in new segments 314 and 315 created from segment 312 of FIG. 1 is similar. Two new segments, 706 in FIGS. 2b and 704 in FIG. 2a, are created by said creation of the two tablettes. New interfaces 708 and 710 lie at the regions at which segments 702 and 706, and 700 and 704, respectively, adjoin.

FIG. 3 demonstrates an immediate release pharmaceutical tablet with an upper segment 322 with a score 328 that is not deep. The tablet remains novel because clear (plain) bottom segment 324 lacks a pharmacologically effective dose of a drug. Interface 326 depicts the region at which the segments adjoin.

\* \* \*

Manufacturing Example

A tablet having a segment containing substantially divided, equal amounts of amlodipine attached to a first segment having no drug is made as follows:

A Stokes 27-station tri-layer rotary tablet press is used. All formulations are directly compressible powder blends. The blending of the amlodipine formulation is performed in a Patterson-Kelly "V" blender. The second segment consists of Nu-Tab® and requires no blending. The tablets are compressed using tablet punches to a hardness of 35 kilopounds. Nu-Tab® is introduced first into a flat bottomed die and compressed to form a second segment. The amlodipine formulation is introduced second into a die to provide a total of 5 mg of amlodipine besylate in each dose. A top die having a wedge shaped embossed top die sized is used to compress the tablet forming ingredients and simultaneously form a deep score that extends into the first segment about of the thickness of said first segment.

| First Segment | Mg. |
| --- | --- |
| Dibasic calcium phosphate anhydrous | 51.13 |
| Amlodipine besylate | 7.15 |
| Sodium starch glycolate (Explotab ®) | 2.48 |
| Magnesium stearate | 0.93 |
| FD&C Blue #1 Aluminum Lake | 0.31 |
| Total | 62.00 |

Manufacturing Instructions
1. Weigh each ingredient.
2. Screen each ingredient.
3. Triturate the color with the major diluent in geometric proportions using a suitable mixer.
4. Add the remaining ingredients, except the lubricant, to the color mixer from step #3 and mix for desired time.
5. Add the lubricant to the blend from Step #4 and mix for desired time.
6. Add the blend to a suitable press fitted with the desired tooling and compress into tablets.

| Second Segment | Mg. |
| --- | --- |
| Nu-Tab ® (Compressible sugar 30/35 N.F.) | 194.00 |

Manufacturing Instructions
1. Weigh each ingredient.
2. Screen each ingredient.
3. Triturate the color with the major diluent in geometric proportions using a suitable mixer.
4. Add the remaining ingredients, except the lubricant, to the color mixer from step #3 and mix for desired time.
5. Add the lubricant to the blend from Step #4 and mix for desired time.
6. Add the blend to a suitable press fitted with the desired tooling and compress into tablets.

Tabletting Instructions
1. Place the powder for amlodipine unitary segments (layer #1) in hopper #1.
2. Place the powder for first segment in hopper #2.
3. Place the powder for active layer in hopper #3.
4. Compress unitary segments to desired weight (tablets for layer #1 should form a soft compact).
5. Compress layer #1 & Layer #2 tablets to desired combined weight of layer #1 and layer #2 weight (tablets should form a soft compact).
6. Compress the bi-layer tablet to the desired total tablet weight (layer #1 weight+layer #2 weight Tablet should be at desired hardness.

DESCRIPTION OF THE PREFERRED EMBODIMENTS

The invention also includes the method of administering one or more drugs via the dosage forms such as tablets and tablettes of the invention to a patient, mammal, or other animal in need of pharmaceuticals for the prevention or treatment of an illness, maintenance of good health, retarding of aging, or other purpose. Included are methods of treating a patient with only one drug from a combination product, such as with a novel tablette of the invention, enabling downward dose adjustment for a variety of reasons; or, in a similar vein, a patient may be treated with one whole tablet containing a plurality of active drugs and in addition receive only one drug from a similar tablet, thus enabling upward dose adjustment. Combination products that can benefit from the invention, in which one drug is in an outer segment, and a second and different drug is in the other outer segment, and an inactive inner segment as in embodiments such as was described in paragraphs 3 and 4 above, include those containing the following pairs of drugs: amlodipine and either benazepril, chlorthalidone, or atorvastatin; benazepril and hydrochlorothiazide; olmesartan and hydrochlorothiazide; and many others, including the majority of the currently-produced combination products. Also included is the method of treating a patient with a precise partial dose of medication from a whole tablet, which may be a half or quarter of the whole dose, but may usefully be a different fraction. Warfarin especially may usefully be produced and dosed according to the invention with separable segments of the tablet that may but need not be as halves, quarters, etc. L-thyroxine and digoxin are other examples that could so benefit, along with warfarin.

The following give possible clinical situations in which the tablets of the invention could provide important benefits.

1. A currently marketed product in the United States is Caduet®, which contains the active ingredients atorvastatin calcium (atorvastatin) and amlodipine besylate (amlodipine) which are largely homogeneously interdispersed in an unscored tablet. The product is indicated to treat both hyperlipidemia (atorvastatin) and hypertension (amlodipine). A patient ingesting this tablet daily may then undergo a blood test and be diagnosed as having liver dysfunction as manifested by elevation of an enzyme's concentration in the blood. The physician may then recommend cessation, possibly temporary, of atorvastatin, which is stated by the manufacturer to be a possible cause of liver dysfunction. A patient receiving Caduet, however, would have to thus also discontinue amlodipine, which is not in this example desired by the physician. A tablet of the invention in which atorvastatin and amlodipine were segregated in different outer active segments, separated by a middle segment of adequate dimensions, would be a clear advance over the current Caduet formulation, because such a tablet would allow a patient to promptly continue ingesting amlodipine while stopping ingestion of atorvastatin, without having to go to a pharmacy and fill a new prescription for a tablet containing only amlodipine as the active ingredient, while having previously had the convenience of having both drugs combined, in a single dosage form. The above embodiment of the invention represents an improvement over the current Caduet dosage form.

Another clinical situation in which the invention is superior to Caduet is one in which a patient receiving amlodipine 5 mg once daily and atorvastatin 20 mg once daily is advised by a physician to increase the daily amlodipine dose to 10 mg once daily. A patient in possession of adequate tablets of the invention, with the active drugs segregated in a three-segment tablet, would be able to promptly increase the amlodipine dose by taking a whole tablet of the invention once daily, plus a tablette containing 5 mg of amlodipine, produced by breaking a second whole tablet of the invention.

Another clinical situation in which the invention is superior to Caduet involves the case in which a physician wishes a patient to ingest atorvastatin 20 mg each morning and amlodipine 2.5 mg twice daily. The invention provides for amlodipine to be separated from atorvastatin and then broken precisely in half. The invention thus allows the patient the advantage of one tablet, whereas to accomplish this currently in the United States would require one 20 mg Lipitor® (atorvastatin) tablet and two Norvasc® (amlodipine) 2.5 mg tablets.

2. The combination of amlodipine besylate and benazepril hydrochloride (benazepril) is marketed in the United States under the brand name of Lotrel®. This product is a capsule that is routinely ingested whole. An embodiment of the invention provides a whole tablet containing one outer segment containing amlodipine as the only active drug and the other outer segment containing benazepril as the only active drug. If desired, either outer layer may be formed into more than one segment, as in FIG. 1a. As in example 1 above regarding Caduet, the middle segment is inactive and may be broken through to create two tablettes, each comprising a whole amount of each outer active segment plus approximately half of the amount of the middle inactive segment. If a patient were to develop a need for double the dose of one active drug but not the other, the tablet of the invention could meet that need. Alternatively, if a patient were to develop a need to ingest only one active drug, possibly temporarily, due to such conditions as blood pressure changes or a side effect to one drug but not the other, the tablet of the invention allows this to be done without a new dosage form being prescribed.

3. Another use of the invention involves the combination of amlodipine and chlorthalidone or another diuretic, which may usefully be combined to treat hypertension. Benefits of the invention are similar to those described in the paragraph immediately preceding this paragraph.

4. Another use of the invention involves the combination of olmesartan medoxomil (olmesartan, an angiotensin receptor blocker) and hydrochlorothiazide (HCTZ). This product is currently marketed in the United States under the name Benicar/HCT®, with the doses, respectively, of, in mg: 20/12.5, 40/12.5, and 40/25. A very common starting dose of a patient will be 20/12.5 once daily. The product is currently marketed in all strengths as a homogeneous tablet containing both active drugs. Formulated according to the current invention, a patient who begins treatment with the 20/12.5 dose may be increased with the same tablet to each of the other doses by ingesting one whole 20/12.5 tablet and either a half tablet containing 20 mg of olmesartan or a half tablet containing 25 mg of HCTZ. This will provide the physician an opportunity to investigate the new dose before giving the patient a new prescription. Other advantages of the invention are similar to those described above.

5. Another useful combination product that may be formulated according to the invention involves angiotensin converting enzyme inhibitors (ACEs) and diuretics such as HCTZ. Both types of drug not uncommonly have side effects, so that the invention will be useful to physicians in dealing with the side effects, as well as with changing dosing needs to deal with the anti-hypertensive and other clinical benefits of the drugs.

6. Another product that may benefit from the invention regarding separating active drugs in separate outer layers with an inactive middle segment (layer) is a combination product containing two active drugs, fluoxetine and olanzapine.

No limitation to the above therapeutic fields or to the specific examples within their fields is intended for tablets of the invention, which may be used in any suitable combination of drugs. No limitation to two-drug combinations exists, as well. For instance, one outer active segment of a tablet according to the invention could contain levodopa and carbidopa, and the other outer active segment could contain entacapone, a tablet product containing all three drugs in a homogeneous fashion that is currently marketed in the United States as Stalevo®. Also, a tablet per the invention could involve five layered segments, with, for example, amlodipine in one outer segment, an inactive segment adjoining it, a middle segment containing chlorthalidone or HCTZ, and a second inactive segment adjoining both it and the other outer segment that contains benazepril (see FIG. 8). If both inactive segments were of adequate dimensions to be conveniently breakable without damaging any of the three active segments, thus providing significant clinical advantages due to the adoption of flexible dosing of the different active segments.

The following list of possible combinations of a plurality of drugs is exemplary and not limiting. The combinations referred to may include two or more members of the classes listed. Drugs listed below, and herein, may for convenience exclude mention of any salt of a drug; e.g., "atorvastatin" is listed even though its marketed form is atorvastatin calcium.

Without limitation, useful combinations may include a plurality of drugs from within the following six drug classes.

In addition, tablets of the invention may be created containing only one of a drug from the following list. With regards to combination use, two methods of use may apply to the invention. One of these methods is to place an individual drug in a granulation and a different individual drug (or combination of drugs) in a different granulation, potentially with an inactive granulation interposed between them; another method is to place a plurality of drugs in one or more segments, 1. Anti-anginal agents, for example:
   A. Calcium antagonists (see list below);
   B. Beta-blocker (see list below);
   C. Organic nitrate preparation (e.g., isosorbide mononitrate or dinitrate).
2. Anti-anginal agent plus an anti-platelet agent, such as aspirin, clopidogrel, or ticlopidine.
3. Two hypoglycemic agents (see list below).
4. Potassium chloride and any thiazide-type or loop diuretic (see lists below).
5. Lipid-lowering agent plus: hypoglycemic agent, anti-platelet agent, anti-anginal agent, and/or antihypertensive agent (see lists above and below)

Hypoglycemic agents include: thiazolidinediones: pioglitazone, rosiolitazone; sulfonylureas: glyburide, glipizide, glimepiride, chlorpropamide;
Biguanides: metformin;
Meglitinides: nateglinide, repaglinide;
Glucosidase inhibitors: acarbose, miglitol.

6. Antihypertensive agents:

Beta-blockers: acebutolol, atenolol, bisoprolol, celiprolol, metoprolol, mebivolol, carvedilol (a mixed alpha-beta blocker), nadolol, oxprenolol, penbutolol, pindolol, propranolol, timolol, betaxolol, carteolol; Calcium antagonists (calcium-channel blockers): nifedipine, amlodipine, verapamil, diltiazem, nisoldipine, felodipine, isradipine, lacidipine, lercanidipine, nicardipine, manidipine;
Thiazide-type diuretics (with or without potassium-retaining diuretics such as triamterene, amiloride, or spironolactone): hydrochlorothiazide, chlorothiazide, cyclopenthiazide, polythiazide, bendrofluazide, hydroflumethiazide, chlorthalidone, indapamide, methylclothiazide, metolazone;
Angiotensin converting enzyme inhibitors: captopril, enalapril, lisinopril, ramipril, trandolapril, quinapril, perindopril, moexipril, benazepril, fosinopril;
Angiotensin receptor blockers: losartan, valsartan, candesartan, telmisartan, eprosartan, irbesartan;
High-ceiling (loop) diuretics (with or without potassium-retaining diuretics such as triamterene, amiloride, or spironolactone): furosemide, torsemide, ethacrynic acid, bumetamide;
Aldosterone antagonist diuretics: spironolactone, eplerenone;
Alpha-blockers: doxazocin, terazosin, prazosin, indoramin, labetolol (a mixed alpha-beta blocker);
Central alpha-agonists: clonidine, methyldopa;
Imidazoline: moxonidine;
Direct vasodilators: hydralazine, minoxidil;
Adrenergic neuronal blocker: guanethidine.
Lipid-lowering agents include:
Statins: lovastatin, simvastatin, pravastatin, rosuvastatin, atorvastatin, fluvastatin;
Fibrates: clofibrate, bezafibrate, fenofibrate, gemfibrozil, ciprofibrate;
Others: ezetimide, niacin, acipimox.

The combinations of drugs disclosed herein are for illustrative purposes and are not intended to limit the scope of the invention.

Regarding the important usage of the tablets and tablettes of the invention, that involving division of a tablet into tablettes containing similar active segments, most drugs that may undergo dosage adjustment will be preferred if they may be divided in an optimally precise manner. Examples of drugs that will especially benefit from the advances of the invention in this manner include narrow therapeutic index drugs such as warfarin, digoxin, L-thyroxine; vasoactive drugs such as amlodipine; hypoglycemic agents such as rosiglitazone and glipizide; and anxiolytics drugs such as alprazolam. These are however but a small fraction of the great mass of drugs that will benefit from the various embodiments and procedures of the invention.

There are numerous methods of use of the dosage forms of the invention, including its tablets and tablettes. Persons skilled in the medical and pharmaceutical arts will recognize the many advantages that the various embodiments of the invention allow over current products. Some examples of benefits of the inventions involving tablets containing exactly one similar active segment are described immediately below.

1. Warfarin is an anticoagulant marketed in the U.S. under the brand name Coumadin®, which is a scored tablet. Research has shown that patients do not break warfarin 5 mg tablets into equal 2.5 mg segments. The invention teaches different types of tablets that allow warfarin tablets of any common human dose to be broken into precise halves, and potentially precise thirds, quarters, etc. (tablettes). Thus a patient may utilize warfarin half-tablets (tablettes) produced as per the invention with similar confidence as in the whole tablet. Because warfarin doses are frequently broken, many clinical scenarios exist in which the invention will benefit patients.

2. Norvasc (amlodipine besylate or amlodipine herein) is marketed as unscored 2.5, 5, and 10 mg tablets in the U.S. These tablets are of irregular shape and are difficult to break. The FDA-approved dosage range is from 2.5 to 10 mg ingested orally daily. The invention allows improved functionality of amlodipine. For example, under the invention, a patient receiving 5 mg daily who a physician wishes to increase to 7.5 mg daily may simply utilize a tablet of the invention that comprises two separate 2.5 mg segments to increase the dose to precisely 7.5 mg, such as by ingesting one whole 5 mg tablet and one 2.5 mg tablette created by breaking a 5 mg tablet into two tablettes each containing 2.5 mg of amlodipine. Convenience and cost savings are clear. Similarly, a patient receiving a 10 mg dose of Norvasc who is advised to reduce the dose to 5 mg daily must currently purchase a new prescription for 5 mg Norvasc tablets. The invention provides the ability to provide a 10 mg tablet that may be broken into two tablettes, each containing precisely 5 mg of amlodipine. The invention may therefore enable greater flexibility of treating patients, and provide cost savings as well. A further benefit of the invention is that various embodiments allow fully accurate separation of a tablet into a tablette comprising one-fourth of the dose of the active ingredient as is found in the whole tablet. This may for example be done for amlodipine by providing four active segments all containing 2.5 mg of amlodipine and all contiguous with the same side of an inactive outer segment (see embodiment #1; and see FIG. 6a modified to have four and not two active segments).

Thus, a 10 mg amlodipine tablet of the invention may be utilized to provide a 7.5 mg dose; or, it may be utilized to provide four 2.5 mg doses.

A further benefit of the invention may relate to pediatric or geriatric doses, which may not be produced in appropriate dose strengths. In the case of amlodipine, a 1.25 mg daily dose may be useful in either small children with hypertension, or in frail elderly patients with angina or hypertension, who may have hepatic dysfunction. Even though the United States Food and Drug Administration (FDA) has not approved a 1.25 mg dose, precise divisibility of the approved 2.5 mg dose would allow a 1.25 mg daily dose. In addition, precise divisibility of the approved 2.5 mg dose will allow accurate dosing of 3.75 mg daily.

Another use of the invention is to enable a method of cost savings for insurers and patients. The invention allows this because many drugs, such as Norvasc and Coumadin, have pricing that differs little (if at all) between different doses. Because tablet splitting is imprecise for most scored tablets, the practice of mandatory splitting has been met with disapproval by most physician and pharmacist organizations. The invention enables tablet splitting because it provides accurate dosing when a tablet (or some tablettes, as in FIG. 1b) of the invention are broken as described herein. Substantial benefits are foreseen from this innovation. In addition, the ability to separate one active drug from another in a combination product has cost saving advantages, as well.

It is recognized that related inventions may be within the spirit of the disclosures herein. Also no omission in the current application is intended to limit the inventors to the current claims or disclosures. While certain preferred and alternative embodiments of the invention have been sec forth for purposes of disclosing the invention, modifications to the disclosed embodiments may occur to those who are skilled in the art.

The invention claimed is:

1. An immediate release compressed pharmaceutical tablet having a first segment that contains a drug or drugs and a second segment, in which: a) said second segment either has no detectable amount of a drug or a pharmacologically ineffective amount of a drug and said tablet consists said first segment and said second segment; or b) said first segment having a score extending at least 70% of the distance from a surface of said first segment, towards an interface between said first and second segments, said surface being in a plane which extends over said score, said distance being measured along a line which is placed at the shortest distance from said plane to the surface of said first segment.

2. An immediate release compressed pharmaceutical tablet as defined in claim 1 in which the distance is from 70% up to 99.5%, and said second segment has no detectable amount of a drug or a pharmacologically ineffective amount of a drug.

3. An immediate release compressed pharmaceutical tablet as defined in claim 2 in which said second segment adjoins a third segment on a face of said second segment, where said face is opposite the interface between said second segment and said first segment.

4. An immediate release compressed pharmaceutical tablet as defined in claim 3 in which said third segment contains the drug or drugs that is or are in said first segment.

5. An immediate release compressed pharmaceutical tablet as defined in claim 3 in which said third segment contains a different drug or drug from that which is or are contained in said first segment.

6. A method of breaking a pharmaceutical tablet as defined in claim 1 which comprises breaking said tablet through a score in which the distance is no less than 70%.

7. A method of breaking a pharmaceutical tablet as defined in claim 1 by breaking through said first segment through said score and also breaking through said second segment.

8. A method of providing a partial dose of a drug contained in an immediate release compressed pharmaceutical tablet as defined in claim 1 which comprises breaking said tablet through the score in said first segment to create a tablette and then administering said tablette to a patient in need of treatment thereof.

9. A pharmaceutical tablet as defined in claim 1 in which said drug or drugs is or are pharmacologically effective in the treatment of cardiovascular conditions, psychiatric conditions, diabetes, thyroid disorders, pain or thrombotic disorders.

* * * * *